United States Patent
Ley et al.

(10) Patent No.: US 12,188,921 B2
(45) Date of Patent: *Jan. 7, 2025

(54) METHOD FOR IN-FIELD DETERMINATION OF WATER TO BINDER RATION OF A CONCRETE MIXTURE

(71) Applicant: THE BOARD OF REGENTS FOR THE OKLAHOMA AGRICULTURAL AND MECHANICAL COLLEGES, Stillwater, OK (US)

(72) Inventors: Matthew Tyler Ley, Stillwater, OK (US); John Bret Robertson, Stillwater, OK (US); Kristopher Jacob LeFlore, Glencoe, OK (US)

(73) Assignee: The Board of Regents for the Oklahoma AGRICULTURAL AND MECHANICAL COLLEGES, Stillwater, OK (US)

(*) Notice: Subject to any disclaimer, the term of this patent is extended or adjusted under 35 U.S.C. 154(b) by 0 days.

This patent is subject to a terminal disclaimer.

(21) Appl. No.: 18/227,594

(22) Filed: Jul. 28, 2023

(65) Prior Publication Data

US 2023/0366871 A1 Nov. 16, 2023

Related U.S. Application Data

(63) Continuation of application No. 16/942,372, filed on Jul. 29, 2020, now Pat. No. 11,740,223.

(60) Provisional application No. 62/879,965, filed on Jul. 29, 2019.

(51) Int. Cl.
*G01N 33/38* (2006.01)
*G01N 5/04* (2006.01)

(52) U.S. Cl.
CPC ............ *G01N 33/383* (2013.01); *G01N 5/045* (2013.01)

(58) Field of Classification Search
CPC ........................... G01N 33/383; G01N 5/045
See application file for complete search history.

(56) References Cited

U.S. PATENT DOCUMENTS

| | | | | |
|---|---|---|---|---|
| 5,520,730 A | * | 5/1996 | Barbour | C04B 7/26 |
| | | | | 106/737 |
| 5,653,552 A | * | 8/1997 | Wiley | E01C 23/14 |
| | | | | 404/95 |
| 6,347,131 B1 | | 2/2002 | Gusterson | |
| 6,889,103 B2 | * | 5/2005 | Martinez | G01N 33/42 |
| | | | | 73/824 |

(Continued)

FOREIGN PATENT DOCUMENTS

| | | |
|---|---|---|
| DE | 102016204332 A1 | 10/2017 |
| EP | 0376865 A2 | 7/1990 |

OTHER PUBLICATIONS

ASTM-C566-13 (Year: 2017).*

(Continued)

*Primary Examiner* — Catherine T. Rastovski
*Assistant Examiner* — Sharad Timilsina
(74) *Attorney, Agent, or Firm* — McAfee & TAft

(57) ABSTRACT

The present disclosure provides methods and apparatus for determining the water content of a fresh concrete mixture. Additionally, the present disclosure provides methods and apparatus for determining the water to binder ratio for a fresh concrete mixture.

17 Claims, 10 Drawing Sheets

Percent Remaining Mass Loss of Concrete Over Time – Configuration 1

(56) References Cited

U.S. PATENT DOCUMENTS

| | | | | |
|---|---|---|---|---|
| 8,220,344 B2 * | 7/2012 | Turpin, Jr. | ............... | G01N 5/04 73/866 |
| 9,278,888 B1 * | 3/2016 | Al-Mutlaq | .............. | C04B 28/04 |
| 2013/0052452 A1 | 2/2013 | Kwangyeol | | |

OTHER PUBLICATIONS

Laboratory Evaluation of . . . water and cement content (Year: 1999).*

DE 102016204332A1 (Year: 2017).*

Abrams, Duff A., Design of Concrete Mixtures, Structural Materials Research Laboratory, Lewis Institute, May 1919, pp. 1-25.

Concrete Manual—A Water Resources Technical Publication, U.S. Dept. of the Interior Bureau of Reclamation, 8th Edition, 1981, Reprinted 1988, pp. 34-39.

Standard Practice for Selecting Proportions for Normal, Heavyweight, and Mass Concrete, ACI Committee 211.1-91, American Concrete Institute Farmington Hills, 1991, pp. 1-38.

Bentz, Evan C., Probabilistic Modeling of Service Life for Structures Subjected to Chlorides, Materials Journal, Title No. 100-M44, Sep.-Oct. 2003, pp. 391-397.

Howdyshell, P.A., Revised Operations Guide for a Chemical Technique to Determine Water and Cement Concrete of Fresh Concrete, Construction Engineering Research Laboratory, Technical Report M-212, Apr. 1977, pp. 1-38.

Whiting, David et al., Laboratory Evaluation of Nuclear Gage for Measurement of Water and Cement Content of Fresh Concrete, ACI Materials Journal, Technical Paper, Title No. 96-M15, 1999, pp. 101-108.

Mancio, Mauricio et al., Instantaneous In-Situ Determination of Water-Cement Ratio of Fresh Concrete, ACI Materials Journal, 107(6), 2010, pp. 1-25.

Wei, Xiaosheng et al., Early Hydration Process of Portland Cement Paste by Electrical Measurement, Journal of Materials in Civil Engineering, 2006, pp. 99-105.

Standard Method of Test for Water Content of Freshly Mixed Concrete Using Microwave Oven Drying, American Association of State Highway and Transportation Officials (AASHTO), 2015, pp. 1-6.

Bickley, John et al., Preparation of a Performance-Based Specification for Cast-in-Place Concrete, RMC Research Foundation, Jan. 2006, pp. 14-18.

Standard Specification for Portland Cement, ASTM Int'l, C150/C150M—19a, 2019, pp. 1-10.

Standard Specification for Concrete Aggregates, ASTM International, C33/C33M—16, 2016, pp. 1-11.

Kosmatka, Steven H. et al., Design and Control of Concrete Mixtures, 14th Edition, Portland Cement Association, 2002, pp. 1-370.

Ley, Tyler M. et al., Determining the Air-Void Distribution in Fresh Concrete with the Sequential Air Method, Construction and Building Materials, 2017, pp. 723-737.

Standard Test Method for Total Evaporable Moisture Content of Aggregate by Drying, ASTM International, 2013, pp. 1-3.

Standard Test Method for Density (Unit Weight), Yield, and Air Content (Gravimetric) of Concrete, ASTM International, 2017, pp. 1-6.

Standard Test Method for Air Content of Freshly Mixed Concrete by the Pressure Method, ASTM International, 2017, pp. 1-10.

Mehta, P. Kumar et al., Concrete Microstructure, Properties, and Materials, Third Edition, McGraw-Hill, 2006, pp. 1-684.

Standard Practice for Sampling Freshly Mixed Concrete, ASTM International, 2017, pp. 1-3.

Standard Practice for Making and Curing Concrete Test Specimens in the Field, ASTM International, 2017, pp. 1-6.

Standard Method of Test for Surface Resistivity Indication of Concrete's Ability to Resist Chloride Ion Penetration, Aashto, TP95-11, 2011, pp. 1-9.

Standard Specifications, Oklahoma Dept. of Transportation (ODOT), 2009, pp. 1-805.

Standard Test Method for Electrical Indication of Concrete's Ability to Resist Chloride Ion Penetration, ASTM International, 2019, pp. 1-8.

Schindler, Anton K. et al., Heat of Hydration Models for Cementitious Materials, ACI Materials Journal, Title No. 102-M04, 2005, pp. 24-33.

Standard Test Method for Asphalt Content of Asphalt Mixture by Ignition Method, ASTM International, 2019, pp. 1-5.

Standard Test Method for Density (Specific Gravity), and Absorption of Coarse Aggregate, ASTM International, 2007, pp. 1-7.

* cited by examiner

METHOD FOR IN-FIELD DETERMINATION OF WATER TO BINDER RATION OF A CONCRETE MIXTURE

CROSS REFERENCE TO RELATED APPLICATION

The present application is a continuation of U.S. patent application Ser. No. 16/942,372 filed on Jul. 29, 2020, which claims priority to U.S. Patent Application Serial No. U.S. Provisional Application No. 62/879,965 filed on Jul. 29, 2019.

BACKGROUND

Concrete has been used as a construction material for more than a century. To ensure longevity of structures prepared from concrete, one must prepare the concrete using the correct water to binder ratio. The slump method is one of the most common methods for determining whether or not the water to binder ratio is proximate to the desired ratio. Unfortunately, the slump method does not provide an accurate assessment of the water to binder ratio. Therefore, the industry would benefit from an accurate assessment of the water to binder ratio. In particular, the industry would benefit from an assessment method that can be carried out at the construction site or where the mixture is created.

SUMMARY

In one aspect, the present invention provides a method for determining the water to binder ratio in a fresh concrete mixture. In another aspect, the present invention provides a method for determining the water content of a fresh concrete mixture.

The method for determining the water content of a fresh concrete mixture begins with the step of providing a test sample of fresh concrete mixture. The fresh concrete mixture comprises binder, water and aggregates. The mass of test sample is determined. Additionally, the method provides for determining the volume of air in the test sample and the absolute volume of the test sample. Using the absorption capacity of the aggregates included in the fresh concrete mixture, the method provides for determining the mass of water contributed by the aggregates to the fresh concrete mixture. Typically, the test sample is formed into generally uniform thickness prior to heating under conditions which will remove all water from the test sample without decomposing the aggregates. Following removal of water from the test sample, the mass of the test sample is again determined and the mass of water removed from the test sample calculated. Finally, the mass of water in the fresh concrete is determined by subtracting the mass of water contributed by the aggregates in the test sample from the mass of water removed by heating the test sample.

The method for determining the water to binder ratio of a fresh concrete mixture begins with the step of providing a test sample of fresh concrete mixture. The fresh concrete mixture comprises binder, water and aggregates. The mass of test sample is determined. Additionally, the method provides for determining the volume of air in the test sample and the absolute volume of the test sample. Using the absorption capacity of the aggregates included in the fresh concrete mixture, the method provides for determining the mass of water contributed by the aggregates to the fresh concrete mixture. Typically, the test sample is formed into generally uniform thickness prior to heating under conditions which will remove all water from the test sample without decomposing the aggregates. Following removal of water from the test sample, the mass of the test sample is again determined and the mass of water removed from the test sample calculated. The mass of water in the fresh concrete is determined by subtracting the mass of water contributed by the aggregates in the test sample from the mass of water removed by heating the test sample. Finally, the water to binder ratio is determined by dividing the mass of water in the test sample of fresh concrete mixture by the mass of the binder in the test sample

DETAILED DESCRIPTION

Figure 1:
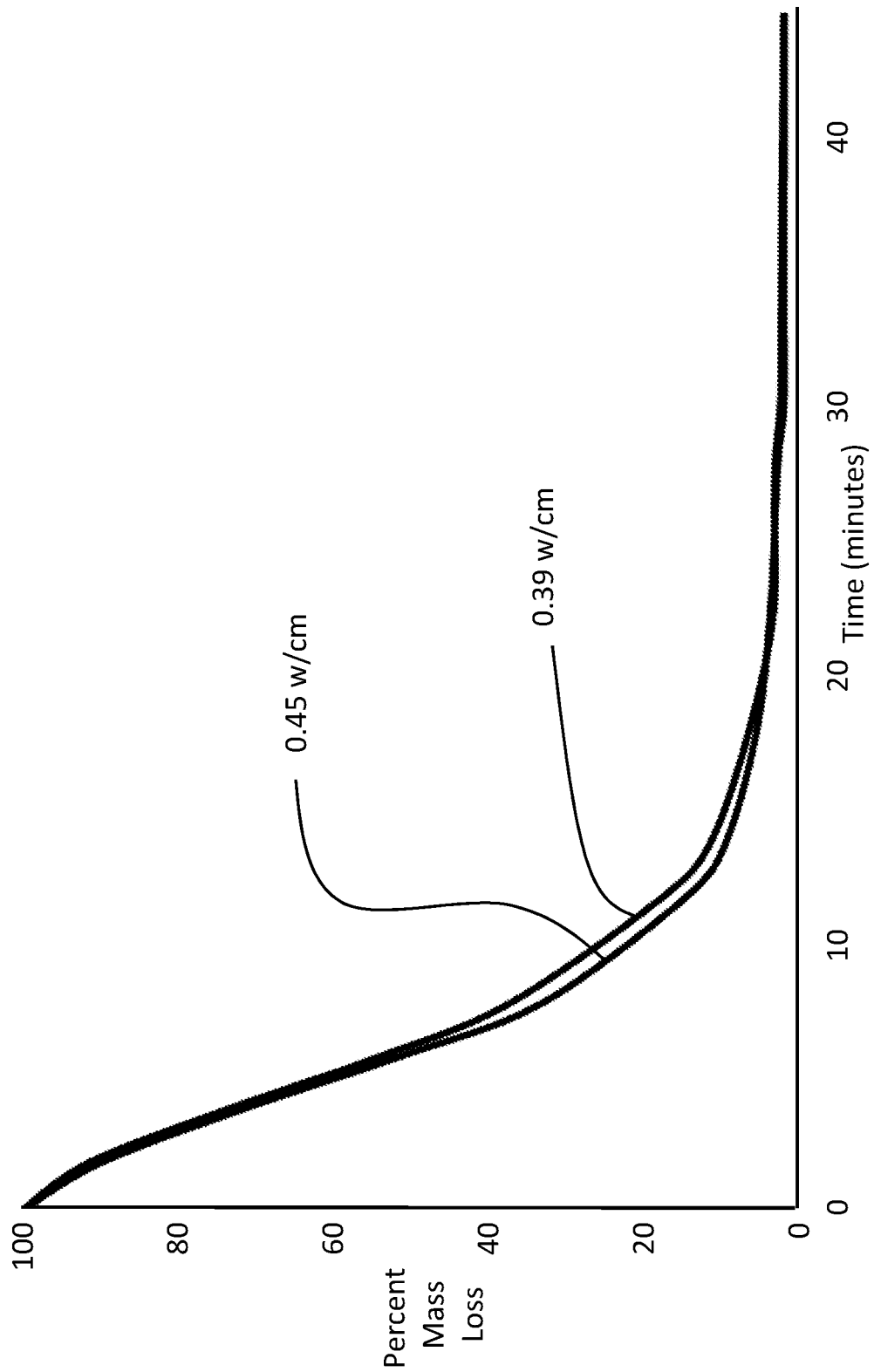
FIG. 1 depicts water loss of two samples when the Test Samples were heated with a pair of heating elements.

The drawings included with this application illustrate certain aspects of the embodiments described herein. However, the drawings should not be viewed as exclusive embodiments. The subject matter disclosed is capable of considerable modifications, alterations, combinations, and equivalents in form and function, as will occur to those skilled in the art with the benefit of this disclosure. In some instances, the term cement has a specific meaning, i.e. Portland Cement. For the purposes of this disclosure, the term binder will be used to represent those cementitious materials capable of undergoing a hydration reaction suitable for preparation of concrete structures.

This disclosure provides methods for determining, in the field, the water content and ultimately the water to binder ratio (w/cm) of concrete mixtures. In most cases, incorrect w/cm have an excess amount of water. In these instances, the resulting concrete structure will have decreased strength and stiffness, increased permeability, and will undergo excess shrinkage during drying. If the excess water produces as little as 0.01 increase in the w/cm ratio, the resulting decrease in strength can be as great as 103 kPa. As a result, structures prepared from this concrete mix will have shorter useful lifespans.

Increasing the w/cm ratio by 0.01 requires only the addition of 0.02 m³ of water per every 6 m³ of binder mix when using 335 kg/m³ of binder. The addition of excess water may occur in a variety of ways, including: leftover wash water, incorrect determination of aggregate moisture content and accidental increase in water to improve workability of the concrete. The method described herein provides the ability to field test the water content or w/cm prior to formation of the designed structure and adjustment of the binder/aggregate component to provide the desired final w/cm.

The described method requires less than 60 minutes to carryout. Typically, following preparation of the Test Sample, the method can be carried out in less than 20 minutes. The time required for performing the method is determined, in part, as described below by the heating mechanism used during the method. In general, use of a portable furnace will reduce the time necessary to perform the described method.

The method for determining the w/cm of a concrete mix will be first described in a stepwise manner and then described in connection with working examples. As this method will normally be practiced at a construction site or place of mixing concrete, the initial step of preparing a concrete mixture will typically occur at a remote location. However, preparation of the concrete mixture may also occur in a controlled environment such as a precast plant, factory, or at a laboratory.

Typical concrete mixtures will contain water, aggregate and a binder, i.e. cementitious component capable of undergoing a hydration reaction with water. Common binder components include, but are not limited to: calcium aluminate, calcium sulfate aluminate, Portland cement, fly ash, slag, silica fume, natural pozzolans and mixtures thereof.

After obtaining a volume of the concrete mixture, the concrete mixture must be formed into a sample suitable for testing. This material will be known as the Test Sample. To permit testing in the field and to reduce testing time, the volume of the Test Sample should be relatively small. In the practice of the present method, no more than 7000 cm³ will be required. In fact, the present w/cm test can be practiced with as little as 1200 cm³ of concrete mixture. Typically, Test Samples having volumes between about 1500 cm³ and about 6000 cm³ will be used to determine the w/cm. Preferably, the Test Sample will have a volume between about 1600 cm³ and about 1900 cm³. To promote uniformity in testing, the method utilizes a mold having a known mass to form the test volume into a Test Sample. If the mold is not suitable for the temperatures required in the test, then the Test Sample will be transferred to a Testing Container. Test results confirming the desired minimum and maximum sample volumes for the Test Sample are reported below after the test examples.

To provide accurate determination of the w/cm, the characteristics of the concrete mixture used to prepare the Test Sample must be either measured or calculated. The following table of variables provides the terms used in the equations provided below.

Table of Variables

| Description | Variable Name |
|---|---|
| Binder specific gravities | $SG_{Binder}$ |
| Coarse aggregate absorptions | $Abs_{Coarse}$ |
| Fine aggregate absorptions | $Abs_{Fine}$ |
| Coarse aggregate specific gravities | $SG_{Coarse}$ |

Table of Variables (continued)

| Description | Variable Name |
|---|---|
| Fine aggregate specific gravities | $SG_{Fine}$ |
| Batched binder masses | $M_{Binder}$ |
| Batched coarse aggregate masses | $M_{Coarse}$ |
| Batched fine aggregate masses | $M_{Fine}$ |
| Batch water mass | $M_{Water}$ |
| Batched volume in mixer | $V_{Batch}$ |
| Batched concrete air volume | $V_{Air}$ |
| Tare mass of mold | $Mold_{Tare}$ |
| Volume of mold | $V_{Mold}$ |
| Mass of mold filled with concrete | $Mold_{Full}$ |
| Mass of mold after emptied | $Mold_{Empty}$ |
| Mass of binder in the Test Sample | $Mold_{Binder}$ |
| Mass of water absorbed in the Test Sample | $Mold_{Water\ Abs}$ |
| Mass of Testing Container (TC) with fresh concrete | $TC_{fresh}$ |
| Mass of Testing Container (TC) with dried concrete | $TC_{Dry}$ |

Following preparation of the Test Sample, the mass of the Test Sample in the mold is determined by subtracting the known mass of the mold from the total mass of the mold plus the Test Sample. Additionally, the volume of air in the Test Sample in the mold must be determined. Methods for determining the volume of air in a concrete sample are well known to those skilled in the art.

Two convenient methods are American Standard Test Method (ASTM) C231 which provides for the determination of the air content of freshly mixed concrete by the Pressure Method and ASTM C138 which provides a theoretical density calculation for the Test Sample based on the materials used to prepare the Test Sample. When using ASTM C231, a separate sample is usually tested, the percent air will be read from the gauge used during testing. Following determination of the percent air in the Test Sample, the volume of air can be readily calculated based on the known dimensions of the Test Sample.

When using ASTM C138, the air volume can be found by using the measured density of the Test Sample and calculating the theoretical density of the Test Sample. The measured density of the Test Sample is compared to the theoretical density as determined based on the components used to prepare the batch of concrete which produced the Test Sample.

The density of the Test Sample in the mold (Mold Density) can be found using the following formula: Mold Density=$(Mold_{Full}-Mold_{Tare})/V_{Mold}$ (Equation 1). Where: $Mold_{Full}$ is the mass of the mold and Test Sample; $Mold_{Tare}$ is the empty weight of the mold; and, $V_{Mold}$ is the volume of the mold which equals the volume of the Test Sample.

The theoretical density of the Test Sample can be defined as: Theoretical Density=total Test Sample mass/Absolute Volume of the Test Sample (Air Free), where total Test Sample mass is determined as described above and is represented by Total Test Sample Mass=$M_{Binder}+M_{Coarse}+M_{Fine}+M_{Water}$ (Equation 2).

The Absolute Volume of the Test Sample (Air Free)= $((M_{Binder})/(SG_{Binder}\times1000))+((M_{Coarse})/(SG_{Coarse}\times1000))+((M_{Fine})/(SG_{Fine}\times1000))+M_{Water}/1000$ (Equation 3). For Equation 3 the masses are considered to be grams. For the theoretical density calculation in lb./ft³, the mass is replaced by batched weight and each 1000 is replaced by 62.4 lb./ft³.

Upon determination of the theoretical density, one can calculate the theoretical air content of the Test Sample by determining the percent difference between the theoretical density and the determined Test Sample density. This calculation is represented as: Air Content (%)=((Theoretical Test Sample Density−Test Sample Density)/Theoretical Test Sample Density)×100 (Equation 4). Following determination of the percent air in the Test Sample, the volume of air can be readily calculated based on the known dimensions of the Test Sample.

The Absolute Volume of the concrete batch mixture used to prepare the Test Sample, with air, must be determined to provide an accurate assessment of the w/cm (referred to Absolute Volume Batch). However, the mathematical expression of the Absolute Volume Batch can be written as: Absolute Volume Batch=$((M_{Binder})/(SG_{Binder} \times 1000)) + ((M_{Coarse})/(SG_{Coarse} \times 1000)) + ((M_{Fine})/(SG_{Fine} \times 1000)) + (M_{Water}/1000) + (V_{Batch} \times (V_{Air}/100)))$ (Equation 5). For Equation 5 the masses are considered to be grams.

Because the w/cm test removes all water from the Test Sample, an accurate calculation of the w/cm requires knowledge of the absorption capacity of the aggregates used to prepare the Test Sample, i.e. the volume of water contributed by the aggregates. Additionally, coarse and fine aggregates absorb water differently. Therefore, different equations are needed to account for the difference in water absorption capacity. The following equation is used for coarse aggregates:

$$\text{Coarse Aggregate Absorbed Water} = (\text{Abs}_{Coarse}/100) \times M_{Coarse} \quad \text{(Equation 6)}.$$

The following equation is used for fine aggregates:

$$\text{Fine Aggregate Absorbed Water} = (\text{Abs}_{Fine}/100) \times M_{Fine} \quad \text{(Equation 7)}.$$

Thus, with knowledge of the absorbed water attributed to both fine and coarse aggregates in the concrete mix used to prepare the Test Sample, one can determine the Total Water Absorbed as reflected by the following:
Total Absorbed Water=Coarse Aggregate Absorbed Water+ Fine Aggregate Absorbed Water (Equation 8). Additionally, when more than one coarse or fine aggregate is used in the concrete mixture, their corresponding water absorption values will be added to the Total Absorbed Water value. Thus, the Total Absorbed Water for the batch of concrete mixture used to prepare the Test Sample can be determined by Equation 8.

Test Sample Density is calculated by taking the sum of the batched masses divided by the absolute volume of the batch. This can be shown mathematically as:
Test Sample Density=Total Test Sample Mass/Absolute Test Sample Volume (Equation 9). This representation also corresponds to Test Sample Density=Eq. 2/Eq. 5. While the Test Sample Density generally corresponds to the value of Equation 1 divided by the known mass, the calculations described here uses all of the batch weights and provides a greater degree of accuracy. Additionally, one will normally compare the two values as a further check on accuracy of the determined Test Sample Density.

The process of removing water from the Test Sample will be explained in detail below. After establishing the mass and volume of the Test Sample in the mold, the Test Sample must be transferred to a Testing Container prior to removing water from the Test Sample. To ensure accurate determination of the w/cm, no more than 10 grams of Test Sample may remain in the mold after removal of the Test Sample. For the purposes of calculating water content or w/cm the mass of the Test Sample originally placed in the mold is used to obtain the volume of the Test Sample that is actually tested. This is calculated because some of the material may have been left within the mold. Thus, Test Sample Volume is represented by: Test Sample Volume=$((\text{Mold}_{Full} - \text{Mold}_{Empty})/(\text{Mold}_{Full} - \text{Mold}_{Tare})) \times V_{Mold}$ (Equation 10).

The total mass of water lost during the test corresponds to the difference between the mass of the Test Sample in the Testing Container (TC) and the mass of the Testing Container with the dry Test Sample. The total mass of water loss is represented as: Water Loss Mass=$TC_{fresh} - TC_{Dry}$ (Equation 11).

The total mass of water lost during the test represents the total water in the Test Sample including the water contributed or absorbed by the coarse and fine aggregates. If the Test Sample is part of a larger batch, then a scale factor will aid in reducing the material weights of the larger batch to the volume of the Test Sample in the mold. This scale factor is identified as: Volume Ratio=Test Sample Volume/Absolute Volume Batch (Equation 12). Thus, Volume Ratio=Eq. 10 divided by Eq. 5. Multiplying the batch weight of a component by the Volume Ratio will represent the weight in the Test Sample for that component.

Thus, the Volume Ratio may be used to determine the weight of the binder, i.e. cement, in the Test Sample based on the corresponding Absolute Volume Batch used to prepare the Test Sample. Therefore, the amount of binder in the Test Sample can be determined by the following equation:

$$\text{Mold}_{Binder} = \text{Volume Ratio} * M_{Binder} \quad \text{(Equation 13)}$$

Where $\text{Mold}_{Binder}$ is the mass of binder in the Test Sample. Further, if the Test Sample is a portion of a larger batch of concrete mixture, then the Volume Ratio will also be used to calculate the total water absorbed ($\text{Mold}_{WaterAbs}$) in the Test Sample. The calculation of $\text{Mold}_{WaterAbs}$ is represented by:

$$\text{Mold}_{WaterAbs} = \text{Volume Ratio} \times \text{Total Absorbed Water} \quad \text{(Equation 14); or,}$$

$$\text{Mold}_{WaterAbs} = \text{Equation 12} \times \text{Equation 8}.$$

Having identified the variables and characteristics of the concrete mixture used to prepare the Test Sample, the method of testing to determine the w/cm can be described. Prior to preparing the Test Sample, the mass and volume of the empty mold to be used are recorded. The mold is filled with fresh concrete mixture to provide the Test Sample. After filling the mold, the mold with the Test Sample is weighed. Following weighing of the mold with the Test Sample, the Test Sample is removed from the mold and placed in a container suitable for heating (Testing Container). After emptying of the mold, the mold is weighed again to ensure that the final weight of the empty mold is within 10 g of the mold prior to filling with the concrete mixture. If the weight variance is within the 10 g tolerance, then the volume of the Test Sample can be determined by Equation 10.

The Test Sample in the Testing Container should have a uniform thickness. According to the present method, the Test Sample should be formed into a uniform thickness between about 6 mm and about 32 mm. The width and length of the Test Sample will be determined by the furnace or other heating device selected for use in the test. Typically, the Test Sample should have a thickness between about 6 mm and about 32 mm, a width between about 200 mm and about 300 mm and a length between about 350 mm and about 450 mm. Preferably, the thickness of the Test Sample will be between 15 mm and 23 mm.

The mass of the Testing Container and the Test Sample is recorded. Then, the Testing Container is placed within an oven or otherwise subjected to heating under a heating element or with the Testing Container sitting on the heating element. Typically, when heating the Testing Container in an oven, the oven will be preheated to a temperature between about 700° C. and about 900° C. More preferably, the oven will be preheated to a temperature between about 800° C. and 830° C.

The actual temperature of heating is not critical to the current method. Rather, complete loss of water is determined by weighing of the Testing Container with the Test Sample. Accordingly, use of a preheated temperature between 100° C. and 1400° C. will reduce the length of the time required to remove all water from the Test Sample. When operating at the higher temperatures, the sample will need to be removed before the aggregates decompose.

The Test Sample is considered to be dry, i.e. free of water, when the weight difference between successive two-minute readings is less than two grams. Upon determination of the complete loss of water based on the two-minute weight readings, the final mass of the Testing Container and Test Sample are recorded. Typically, when heating within an oven, the test time will require about 10 minutes to 20 minutes. More commonly, performing the test in an oven will require about 12 minutes.

When carrying out the test using one or two heating elements, the method does not have a time limit. Rather, the Testing Container can be left on or under the heating element(s) and subsequently weighed at any time after about 30 minutes. This allows other tasks to be performed during the testing and do not have to be immediately measured when all of the water is removed. This is discussed in more detail later in the document. FIG. 1 depicts the loss of mass for two samples when the Testing Container was placed on a 1500 Watt hot plate and a heating element located above the Test Sample.

Following removal of water by heating, the w/cm can be calculated. The weight loss after heating represents the total water loss from the Test Sample, including absorbed water in the aggregates (fine and coarse). Thus, to determine the water content or w/cm the calculation must account for water that should be part of the aggregate. Total water loss mass minus the aggregate absorbed water ($Abs_{Coarse}$+$Abs_{Fine}$) mass represents the adjusted water loss. Thus, the method for determining the w/cm will also provide the total water content and the adjusted water content in the Test Sample and provides the ability to determine the total water in the batch. The w/cm can then be determined by subtracting the $Mold_{WaterAbs}$ mass from the total water loss mass and dividing by Mold binder mass. Thus, the equation for the measured w/cm is:

$$\text{Measured w/cm} = (\text{Water Loss Mass} - \text{Mold}_{WaterAbs})/(\text{Mold}_{Binder}) \quad \text{(Equation 15)}.$$

Equation 15 can also be represented by: Measured w/cm= (Eq. 11–Eq. 14)/Eq. 13. The measured w/cm is a result of the test method described above. The measured w/cm can be compared with the w/cm of the batch of concrete (Batch w/cm) used to prepare the Test Sample. The Batch w/cm is calculated by dividing the $M_{Water}$ by $M_{Binder}$. The total water loss may also be a useful measure in this test as a method of quality control.

In an alternative embodiment, the method can be carried out using an oven with an integrated scale. When heating the Test Sample with an oven or other heating element having the ability to monitor Test Sample weight in real-time, the operating temperature can be increased to temperatures greater than the decomposition temperatures of the components making up the concrete in order to reduce testing time. By continuous monitoring of the Test Sample weight, one can determine the complete loss of water from the Test Sample prior to the individual components of the Test Sample undergoing decomposition due to excessive heat. The temperature and rate of thermal decomposition of concrete components are well known as evidenced by the following:

| Temperature Range | Description of Heat Changes in Fresh Concrete |
|---|---|
| 20-200° C. | Capillary water loss and reduction in cohesive forces as water expands<br>Ettringite dehydration (80-150° C.)<br>C—S—H dehydration (135-150° C.)<br>Gypsum decomposition (150-170° C.)<br>Calcium monosulfate dehydration (185-200° C.) |
| 300-400° C. | Decomposition of some siliceous aggregates (350° C.) |
| 400-500° C. | Portlandite decomposition (460-540° C.)<br>$Ca(OH)_2 \rightarrow CaO + H_2O$ |
| 600-800° C. | Further C—S—H dehydration due to phase change (600-750° C.) |
| 800-1000° C. | Dolomite decomposition (840° C.)<br>Calcite decomposition (930-960° C.)<br>$CaCO_3 \rightarrow CaO + CO_2$, carbon dioxide release |
| 1200-1300° C. | Concrete components begin melting |
| 1300-1400° C. | Remaining binder-based composite exists only in a liquid state |

Figure 9:
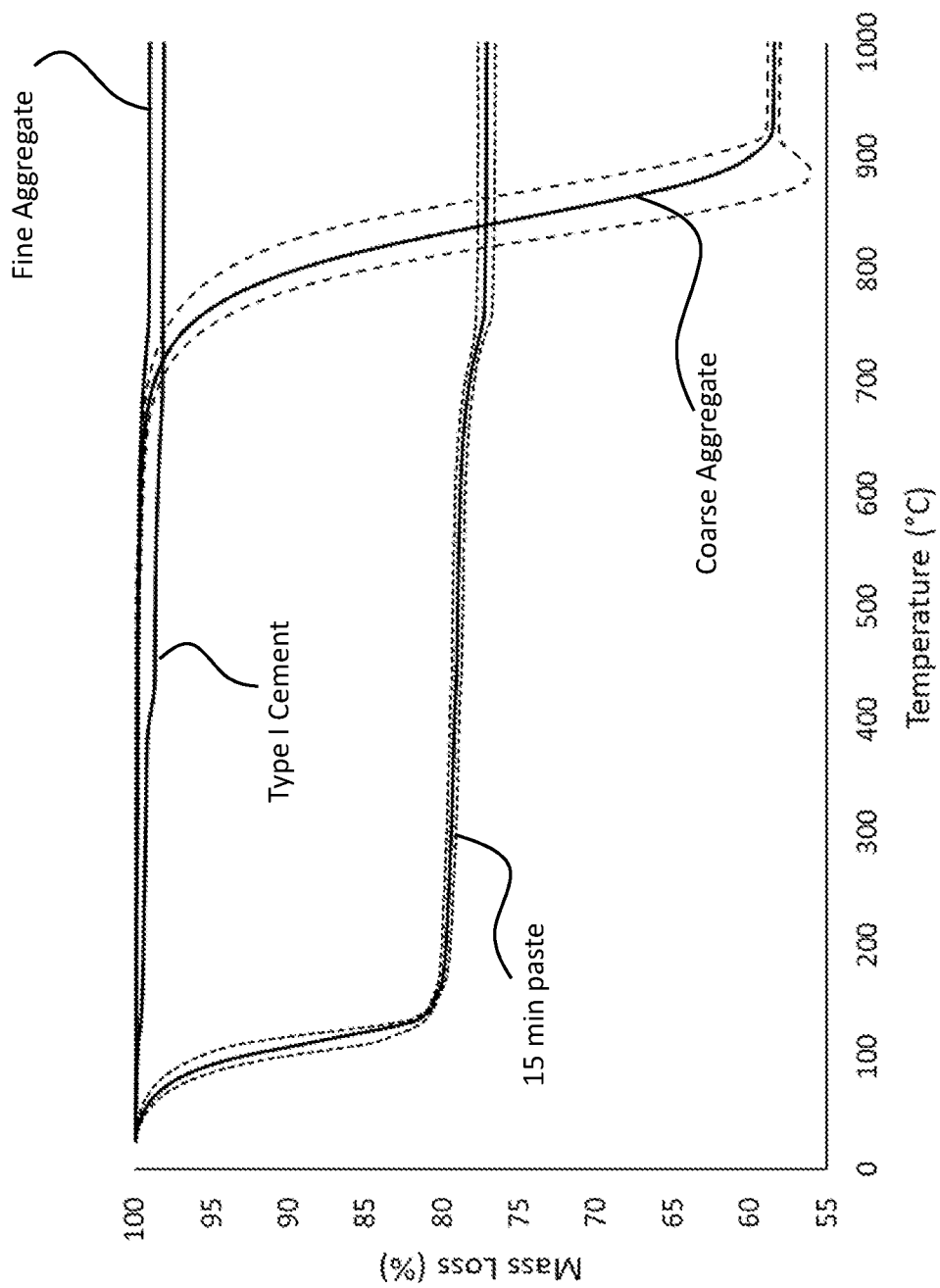
FIG. 9 depicts the loss of mass due to decomposition of the indicated materials.
Figure 10:
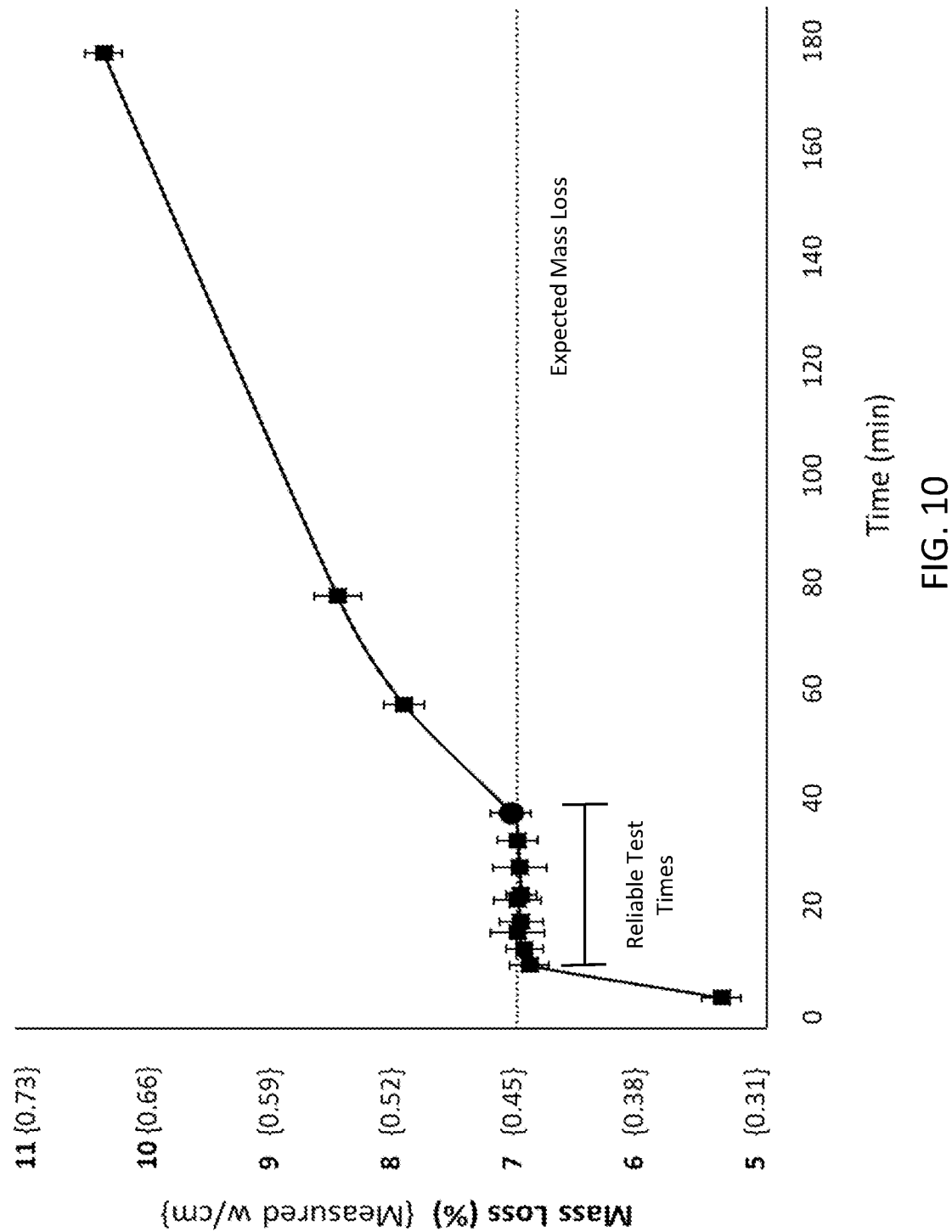
FIG. 10 depicts a mass loss curve over time for a concrete mixture containing limestone 1 in an oven set at 815° C.

Additionally, FIGS. 9-10 depict the loss of mass relative to temperature and time. FIG. 9 depicts the loss of mass from paste, binder, coarse aggregate and fine aggregate when performing thermogravimetric analysis. The solid lines represent the average of the specific material tested with the dashed lines representing the upper and lower standard deviation from the average. The anhydrous Portland cement and fine aggregate show less than 2% mass loss up to 700° C. The fresh paste loses 20% of the mass at 135° C. and then another 4% at 700° C. For temperatures>700° C., the mass loss for the paste is <2%. However, from 600° C. to 900° C., the coarse aggregate has a mass loss of 40% from thermal decomposition. This is likely from $CO_2$ leaving limestone 1.

To determine the permissible time period for heating of a sample, a limestone 1 concrete mixture was tested within an oven at a temperature of 815° C. As reflected by FIG. 10, an initial mass loss occurs over the first 10 minutes within the oven from the water. Subsequently, the mass of the sample remains substantially constant until 40 minutes has passed. After 40 minutes additional mass loss due to decomposition begins from the aggregate. The time to decomposition for common aggregates can readily be determined. The following table provides examples of decomposition time for select coarse aggregate at 600° C.

| Coarse Aggregate Type | Time of Decomposition (min) |
|---|---|
| Dolomitic Limestone | 40 |
| Gabbro | 50 |
| Glacial Till 1 | 40 |
| Glacial Till 2 | 45 |
| Granite 1 | 40 |
| Limestone 1 | 40 |
| Limestone 2 | 45 |
| Quartzite-Granite 1 | 45 |
| Quartzite-Granite 2 | 50 |
| Sandstone | 45 |

Thus, with knowledge of the decomposition time for the aggregate and other components within the concrete batch, one can determine the w/cm and water content at temperatures greater than the decomposition temperature of the concrete batch components. In order to practice the high temperature w/cm and/or water content analysis, a high temperature oven or other heating device and scales compatible with the same will be required. During heating to remove water from the Test Sample, the weight will be constantly monitored and recorded. As reflected by FIG. 10, the resulting graph of mass in the Testing Container will reflect a plateau corresponding to the mass of the Test Sample minus all water. As the components of the Test Sample begin to decompose, the slope of the graph will begin to climb reflecting the loss of aggregate material. Higher temperatures are valuable because they will remove evaporable water from the sample at a higher rate and this can shorten the length of the test as long as it does not cause the aggregate to explode. The aggregates will explode if enough water vapor is trapped in the torturous internal pore structure of the aggregates. This issue can be addressed by using a sufficient lid on the testing containers.

The degree of hydration is a measure of the extent of the reactions between the cementitious materials and the water. The degree of hydration is defined as the ratio of the amount of reacted binder divided by the amount of binder added during mixing. The degree of hydration is a useful parameter because it indicates the amount of reaction that has taken place. Additionally, the degree of hydration corresponds to the amount of heat given off or the development of physical properties like the change in stiffness, strength, or decrease in porosity of the concrete. Further, the degree of hydration is proportional to the amount of water that has reacted with cement and is no longer available for reaction or evaporation. The water that is no longer available is known as bound water.

The most common techniques to determine the degree of hydration include measuring a parameter at a certain point in the reaction and comparing it to either the theoretical total amount or a measured amount from a mature sample. Some methods to do this include measuring: the total heat of hydration, the amount of chemically combined water, the amount of calcium hydroxide present in the paste, the specific gravity of the cement paste, the surface area of the cement paste, the amount of anhydrate cement present in the paste, the strength development or maturity, and the dielectric properties of the concrete. Other methods may also exist.

In this work, the degree of hydration will be determined by first estimating the total amount of heat released by the full reaction of the binder. The total heat of hydration for Portland cement can be quantified by the following equation:

$$H_{cem} = 500 \times C_3S + 260 \times C_2S + 866 \times C_3A + 420 \times C_4AF + 624 \times SO_3 + 1186 \times FreeCaO + 850 \times MgO \quad \text{(Equation 16)}$$

Where $H_{cem}$ is the total heat of hydration of the binder (J/g). The other variables in Equation 16 are the weight ratio for each compound in the Portland cement binder. These compounds are abbreviated with cement chemistry shorthand where $C_3S$ is tricalcium sililcate, $C_2S$ is dicalcium silicate, $C_3A$ is tricalcium aluminate, and $C_4AF$ is calcium alumino ferrite. Thus, for example, as used in Equation 16, $C_3S$ represents the weight ratio of tricalcium sililcate. Other equations exist to determine the total heat of hydration for different binders that one skilled in the art will recognize and be able to apply in the described method.

The total heat of hydration can then be compared to the measured total heat at any given time during the reaction of the mixture to obtain the degree of hydration at that point in time. This can be expressed mathematically as:

$$\text{Degree of Hydration (\%)} = \frac{H(t)}{H_{cem}} * 100 \quad \text{(Equation 17)}$$

Where H(t) is the cumulative heat of hydration released at time t (J/g) and $H_{cem}$ is the total heat of hydration of the binder (J/g).

Figure 8:
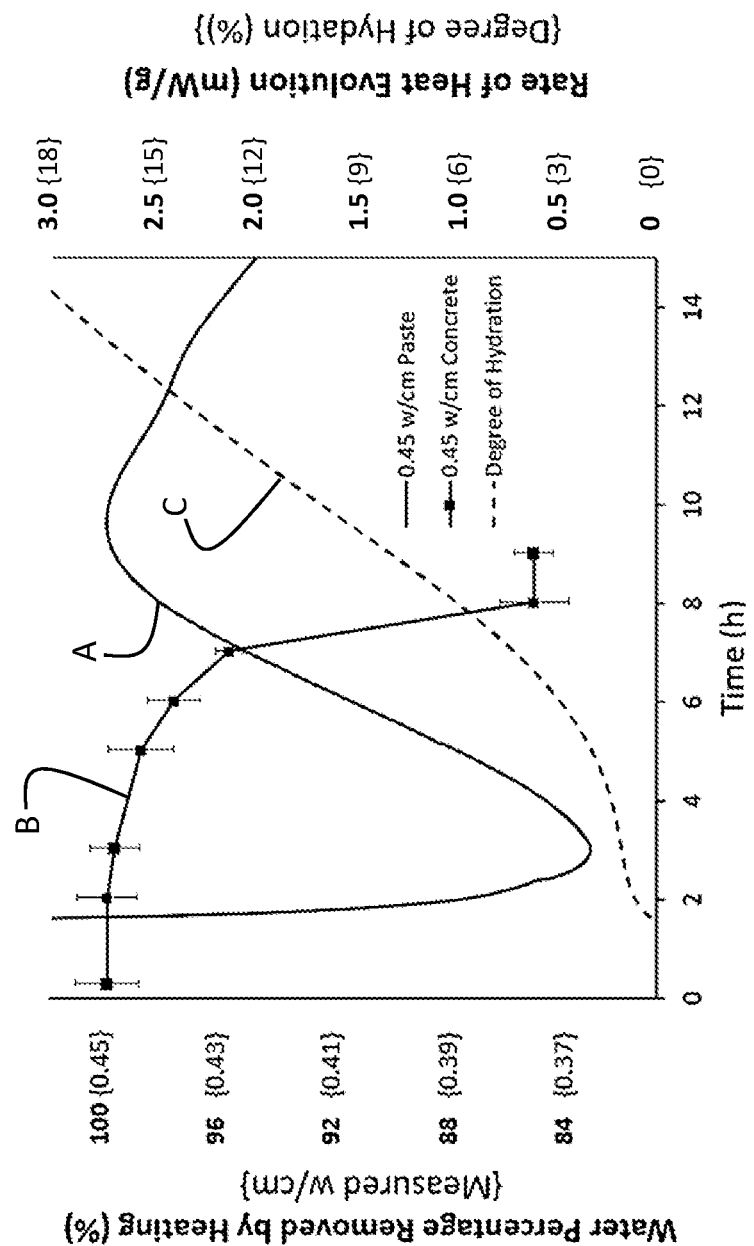
FIG. 8 depicts as line A the rate of heat change from isothermal calorimetry values over time as the hydration reaction between the binder component and water progresses and depicts the change in the water content and w/cm over time for concrete as line B. Line C shows the degree of hydration in the reaction.

FIG. 8 shows the amount of water removed and the estimated w/cm on the left axis and the rate of heat change and the degree of hydration on the right axis compared to the length of time of the reaction. The total heat of hydration for the cement in FIG. 8 calculated to be 473 J/g according to Equation 16.

FIG. 8 demonstrates that the method for determining w/cm and water content can be performed with suitable accuracy up to about five hours after preparation of the master batch of concrete. In FIG. 8, Line A reflects the rate of heat evolution over time generated by the hydration reaction. Line B reflects the measured w/cm of a concrete formulated to have a w/cm of 0.45 and Line C reflects the degree of hydration. As reflected by Line B, the heat of reaction does not have a negative effect on the measured w/cm until five hours had passed. This corresponds to a degree of hydration of approximately 2%. Thus, the methods of determining w/cm and/or water content should preferably be performed within five hours of preparing the concrete at the batch plant or at a degree of hydration of less than 2%. The degree of hydration is an important parameter to use in this comparison as it provides direct insight into the amount of reaction that occurs when different measurements are made.

Test Results

The foregoing method has been tested using a combination of heating elements with one heating element located above the Testing Container housing the Test Sample and a second heating element under the Testing Container. This configuration of heating elements is referred to herein as Configuration 1. In the following test results, the heating element located above the Testing Container was operated at a temperature of about 700° C. The heating element on which the Testing Container rested was operated at its maximum output of 1500 Watts. The Testing Container had a diameter of 23 cm with a depth of 8 cm.

Figure 2:
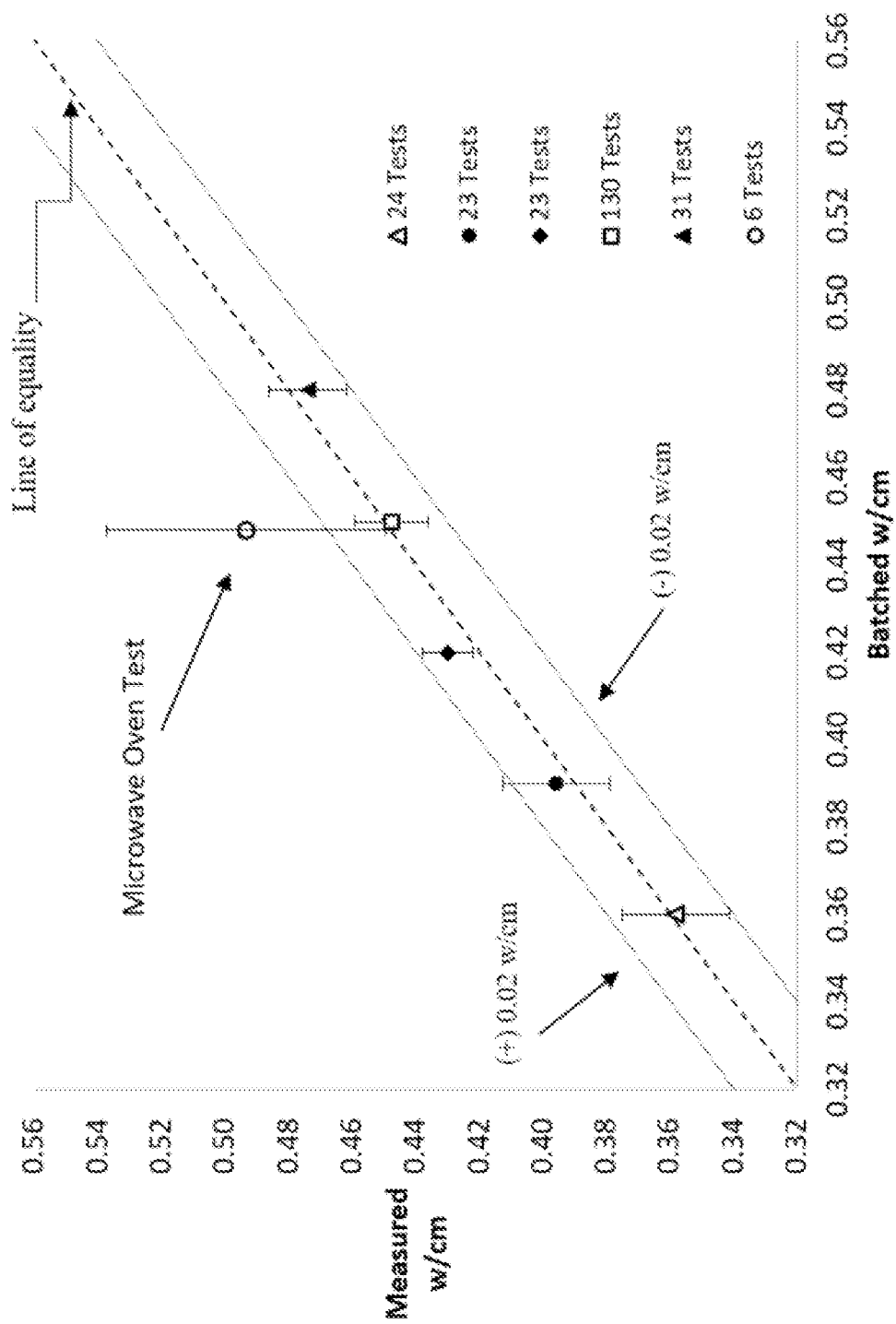
FIG. 2 depicts the test results of Table 1 when heating the Test Samples with a pair of heating elements.
Figure 3:
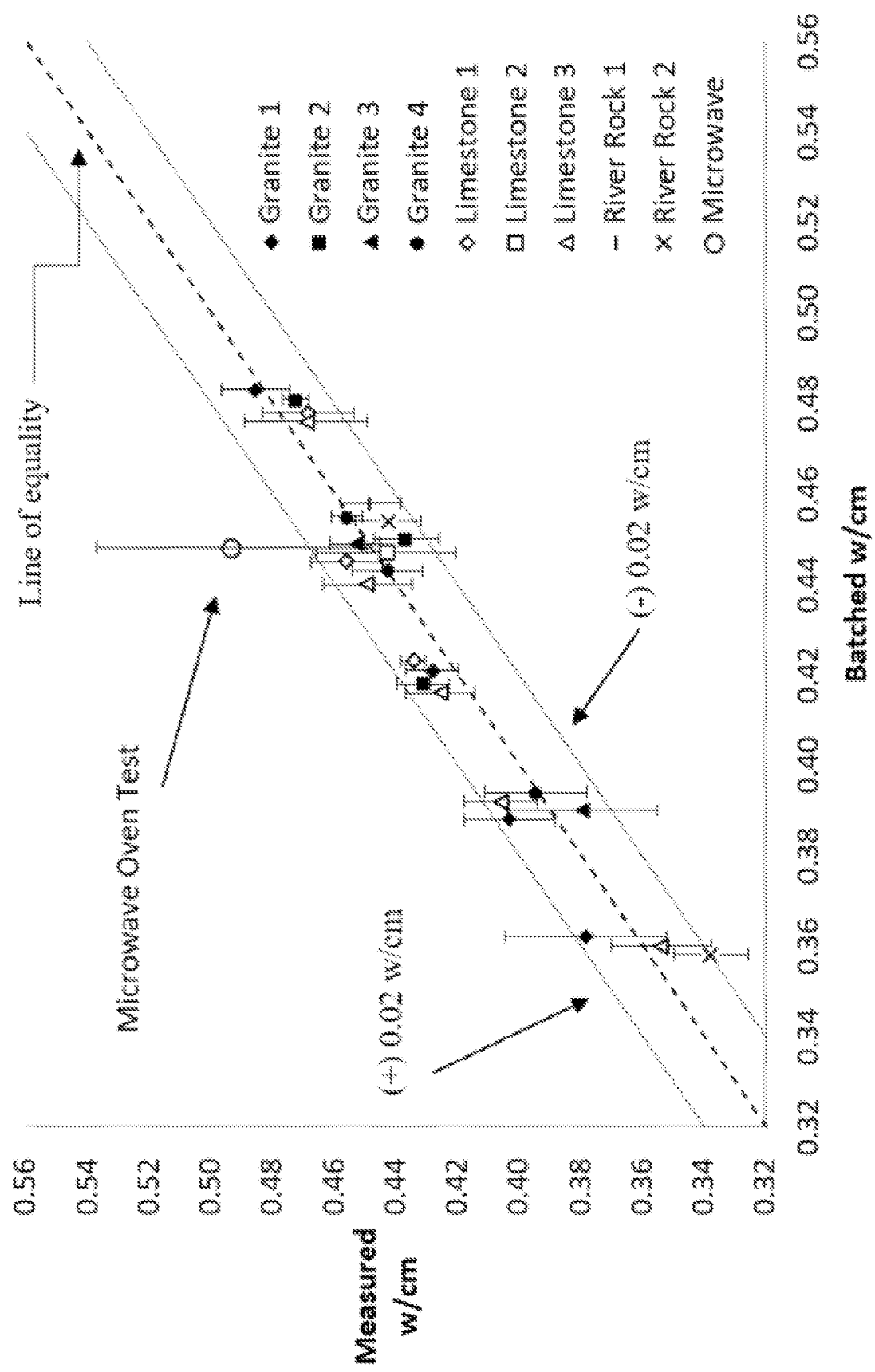
FIG. 3 depicts the test results of Table 1 grouped by mixture.

Configuration 1 was initially tested using 231 lab mixtures of concrete as reported in Table 1 below. FIG. 2 depicts the average and one standard deviation for each measured w/cm versus the calculated batched w/cm. For the purposes of FIG. 2, the data has been combined for each w/cm. A line of equality is included in FIG. 2 to show an exact match of the batched and the measured w/cm. The two lines on either side represent a +/−0.02 w/cm. This shows a reasonable range for the w/cm variation. Testing performed according to a prior art method using a microwave was done on limestone 1 aggregate and a natural sand 1. The results of this test are also shown in FIG. 2. FIG. 3 uses the same data as FIG. 2; however, the FIG. 3 provides the data as individual mixture combinations.

TABLE 1 summary of fresh w/cm sorted by coarse aggregate, Configuration 1

| Tests | Batched w/cm | Average Measured w/cm | Difference Batched and Measured | Standard deviation | COV (%) | Coarse Aggregate Type | Fine Aggregate Type |
|---|---|---|---|---|---|---|---|
| 4 | 0.36 | 0.38 | −0.020 | 0.026 | 6.9 | Granite 1 | Natural Sand 1 |
| 13 | 0.36 | 0.36 | 0.000 | 0.013 | 3.5 | Limestone 1 | Natural Sand 1 |
| 3 | 0.36 | 0.35 | 0.010 | 0.010 | 2.9 | Limestone 1 | Natural Sand 2 |
| 4 | 0.36 | 0.34 | 0.020 | 0.012 | 3.6 | River Rock 2 | Natural Sand 1 |
| 11 | 0.39 | 0.40 | −0.010 | 0.015 | 3.6 | Granite 1 | Natural Sand 1 |
| 4 | 0.39 | 0.38 | 0.010 | 0.024 | 6.4 | Granite 3 | Natural Sand 1 |
| 4 | 0.39 | 0.39 | 0.000 | 0.017 | 4.2 | Granite 4 | Natural Sand 1 |
| 4 | 0.39 | 0.41 | −0.020 | 0.012 | 2.9 | Limestone 1 | Natural Sand 1 |
| 6 | 0.42 | 0.43 | −0.010 | 0.008 | 2.0 | Granite 1 | Natural Sand 1 |
| 6 | 0.42 | 0.43 | −0.010 | 0.008 | 1.9 | Granite 2 | Natural Sand 1 |
| 7 | 0.42 | 0.43 | −0.010 | 0.011 | 2.6 | Limestone 1 | Natural Sand 1 |
| 4 | 0.42 | 0.43 | −0.010 | 0.004 | 0.9 | Limestone 3 | Natural Sand 1 |
| 8 | 0.45 | 0.44 | 0.010 | 0.011 | 2.5 | Granite 1 | Natural Sand 1 |
| 2 | 0.45 | 0.43 | 0.020 | 0.012 | 2.7 | Granite 1 | Mfg. Sand |
| 4 | 0.45 | 0.44 | 0.010 | 0.009 | 2.0 | Granite 1 | Natural Sand 2 |
| 7 | 0.45 | 0.44 | 0.010 | 0.011 | 2.4 | Granite 2 | Natural Sand 1 |
| 6 | 0.45 | 0.45 | 0.000 | 0.008 | 1.8 | Granite 3 | Natural Sand 1 |
| 4 | 0.45 | 0.46 | −0.010 | 0.005 | 1.1 | Granite 4 | Natural Sand 1 |
| 65 | 0.45 | 0.45 | 0.000 | 0.015 | 3.2 | Limestone 1 | Natural Sand 1 |
| 16 | 0.45 | 0.44 | 0.010 | 0.023 | 5.1 | Limestone 2 | Natural Sand 1 |
| 6 | 0.45 | 0.46 | −0.010 | 0.012 | 2.5 | Limestone 3 | Natural Sand 1 |
| 6 | 0.45 | 0.45 | 0.000 | 0.010 | 2.2 | River Rock 1 | Natural Sand 1 |
| 6 | 0.45 | 0.44 | 0.010 | 0.011 | 2.4 | River Rock 2 | Natural Sand 1 |
| 7 | 0.48 | 0.49 | −0.010 | 0.011 | 2.3 | Granite 1 | Natural Sand 1 |
| 4 | 0.48 | 0.47 | 0.010 | 0.004 | 0.9 | Granite 2 | Natural Sand 1 |
| 10 | 0.48 | 0.47 | 0.010 | 0.015 | 3.1 | Limestone 1 | Natural Sand 1 |
| 10 | 0.48 | 0.47 | 0.010 | 0.020 | 4.2 | Limestone 3 | Natural Sand 1 |

In Table 1, the average for the column Difference Batched and Measured was 0.001. Accordingly, very little difference exists, on average, between batched and measured w/cm. The average standard deviation for all measured w/cm for the 231 mixtures is 0.012 for w/cm between 0.36 and 0.48 for a variety of different materials. The average coefficient of variation (COV) for all the tests is 3.0%. Thus, the method for determining the w/cm of fresh concrete is highly accurate. Further, FIG. 2 reflects that aggregate type and w/cm do not seem to influence the results for the materials and mixtures investigated. In contrast, current microwave testing in accordance with AASHTO T 318 standards typically have differences between measured and batched w/cm of about 0.45 with standard deviations of about 0.044 w/cm and a COV of about 8.9%. Additionally, when carrying out the microwave test, the operator must stop the heating process in order to break up the sample to ensure removal of all water from the sample. Thus, the present method not only provides results that have standard deviations approximately three time smaller than the standard deviation of the currently practiced microwave oven test; but also, provides a more efficient hands-off test.

Configuration 1 was also tested in the field. Table 2, provided below, contains the test results for the field tests. The standard deviation and COV values were based on two samples taken and tested per truck.

TABLE 2

Field Testing using batches obtained from Trucks, Configuration 1

| Truck Number | Batched w/cm | Average Measured w/cm | Difference Batched and Measured | Standard deviation | COV (%) |
|---|---|---|---|---|---|
| Truck 1 | 0.42 | 0.43 | −0.01 | 0.005 | 1.2 |
| Truck 2 | 0.45 | 0.45 | 0.00 | 0.009 | 2.0 |
| Truck 3 | 0.47 | 0.46 | 0.01 | 0.004 | 1.0 |
| Truck 4 | 0.44 | 0.44 | 0.00 | 0.013 | 3.0 |
| Truck 5 | 0.44 | 0.44 | 0.00 | 0.004 | 1.0 |
| Truck 6 | 0.43 | 0.47 | −0.04 | 0.002 | 0.5 |
| Truck 7 | 0.42 | 0.42 | 0.00 | 0.003 | 0.8 |
| Truck 8 | 0.42 | 0.42 | 0.00 | 0.007 | 1.7 |
| Truck 9 | 0.43 | 0.44 | −0.01 | 0.003 | 0.6 |
| Truck 10 | 0.39 | 0.39 | 0.00 | 0.007 | 1.8 |
| Truck 11 | 0.39 | 0.39 | 0.00 | 0.002 | 0.6 |
| Truck 12 | 0.39 | 0.39 | 0.00 | 0.004 | 1.0 |
| Truck 13 | 0.44 | 0.46 | −0.02 | 0.002 | 0.5 |
| Truck 14 | 0.44 | 0.46 | −0.02 | 0.016 | 3.4 |
| Truck 15 | 0.44 | 0.48 | −0.04 | 0.006 | 1.2 |
| Truck 16 | 0.43 | 0.43 | 0.00 | 0.006 | 1.3 |
| Truck 17 | 0.42 | 0.43 | −0.01 | 0.008 | 1.8 |
| Truck 18 | 0.43 | 0.44 | −0.01 | 0.007 | 1.6 |
| Truck 19 | 0.36 | 0.38 | −0.02 | 0.003 | 0.9 |
| Truck 20 | 0.48 | 0.49 | −0.01 | 0.005 | 1.0 |
| Truck 21 | 0.48 | 0.44 | 0.04 | 0.002 | 0.4 |
| Truck 22 | 0.37 | 0.38 | −0.01 | 0.006 | 1.4 |
| Truck 23 | 0.44 | 0.42 | 0.02 | 0.005 | 1.2 |

TABLE 2-continued

Field Testing using batches obtained from Trucks, Configuration 1

| Truck Number | Batched w/cm | Average Measured w/cm | Difference Batched and Measured | Standard deviation | COV (%) |
|---|---|---|---|---|---|
| Truck 24 | 0.50 | 0.54 | −0.04 | 0.001 | 0.2 |
| Truck 25 | 0.49 | 0.46 | 0.03 | 0.003 | 0.7 |
| Truck 26 | 0.42 | 0.42 | 0.00 | 0.001 | 0.3 |
| Truck 27 | 0.43 | 0.45 | −0.02 | 0.003 | 0.8 |

Figure 4:
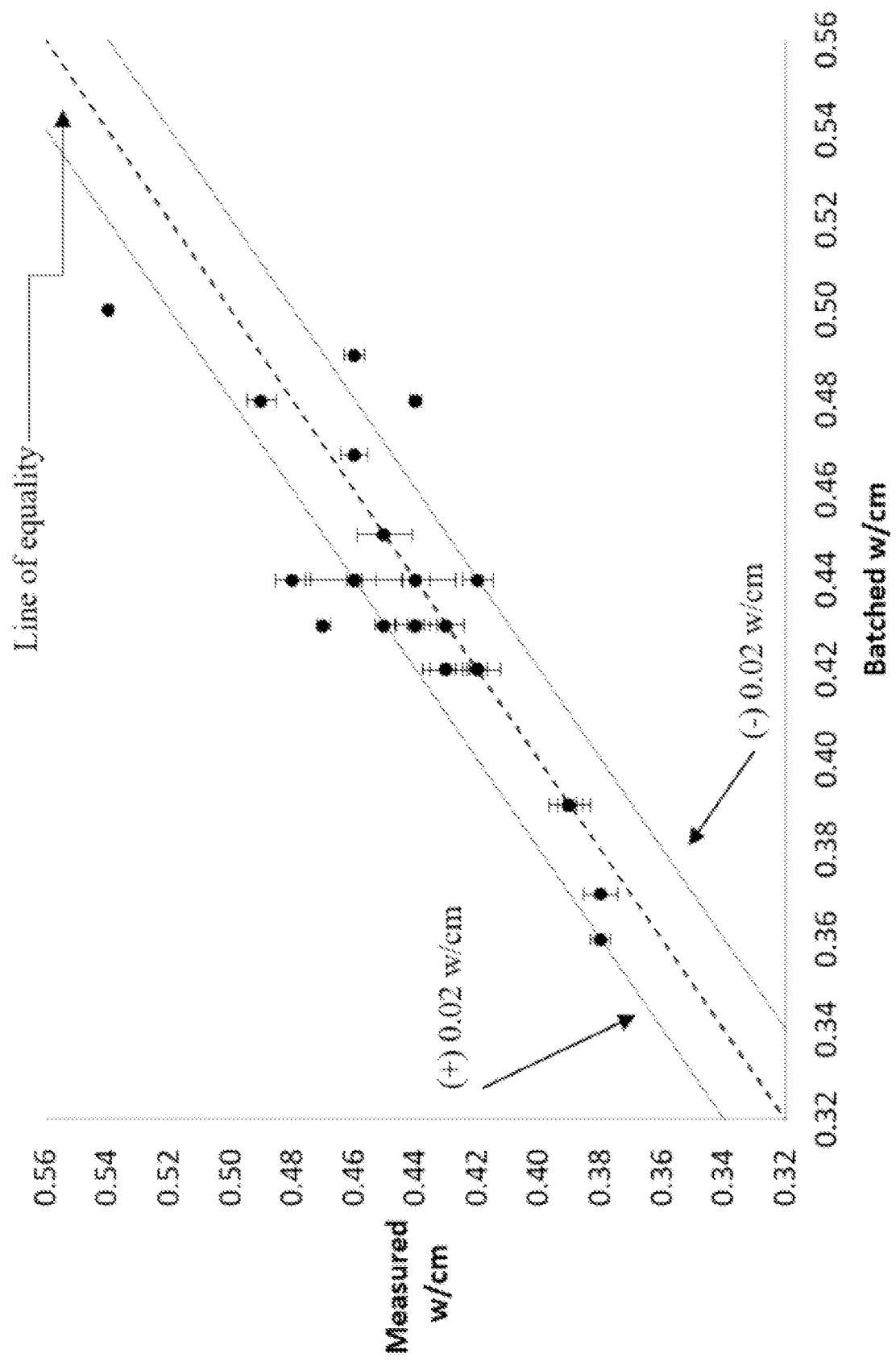
FIG. 4 depicts the test results of field testing depicted in Table 2 when heating the Test Samples with a pair of heating elements.

The data from Table 2 compares favorably to the data obtained from the laboratory test samples. In particular, the average standard deviation for Table 2 is 0.010 which is very close to the 0.012 standard deviation of Table 1. Further, the COV for Table 2 is 1.2% which is actually lower than the 3.0% obtained in Table 1. While the field testing used fewer samples, the results are clearly favorable and reflect the degree of accuracy necessary for use in the field to ensure the desired w/cm. FIG. 4 graphically depicts the data of Table 2. Finally, Table 2 demonstrates that 15% of the field mixtures had a batched w/cm 0.02 higher than the designed w/cm information provided by the batch plant. This was obtained from trucks at the batch plant and does not reflect the additional water that could be added before placement within the forms. Furthermore, these samples were not taken randomly.

Table 3 below demonstrates the potential usefulness of the new method for testing the w/cm. In view of the lack of a testing method for fresh concrete, current specifications limit maximum slump of concrete to 18 cm over concerns of excess water. In this instance, batch samples from Trucks 6 and 7 experienced slump greater than the accepted limit. However, after testing both samples using the new field method for determining w/cm, the sample from Truck 7 was found to be within the acceptable w/cm range. Thus, the new method for testing the w/cm can reduce the number of rejected concrete loads while more accurately identifying those loads that fail to meet specifications.

TABLE 3

Field Testing Comparison of Slump Test Results to New Method for w/cm results

| Truck Number | Batched w/cm | Avg. Measured w/cm | Measured Slump (cm) | Air Content (%) | Specified w/cm | Max. Slump (cm) | Specified Air Content (%) |
|---|---|---|---|---|---|---|---|
| Truck 6 | 0.43 | 0.47 | 23 | 4.7 | 0.25-0.44 | 18 | 6 ± 1.5 |
| Truck 7 | 0.42 | 0.42 | 20 | 8.1 | 0.25-0.44 | 18 | 6 ± 1.5 |

Table 4 provided below provides the characteristics of the concrete for each sample Truck.

TABLE 4

Concrete Sample by Truck

| Truck | Batch Size (m³) | Binder (kg) | Fly Ash C (kg) | Fly Ash F (kg) | Slag (kg) | Coarse (kg) | Fine (kg) | Water (kg) |
|---|---|---|---|---|---|---|---|---|
| 1 | 10.5 | 2533 | 628 | | | 7140 | 7203 | 159 |
| 2 | 10.5 | 2712 | | | | 8500 | 6586 | 147 |
| 3 | 10 | 2549 | | | | 8110 | 6232 | 143 |
| 4 | 10 | 2545 | | | | 8410 | 5679 | 135 |
| 5 | 10 | 2545 | | | | 8509 | 5652 | 133 |
| 6 | 10 | 2554 | | | | 8428 | 5724 | 133 |
| 7 | 10 | 2549 | | | | 8373 | 5697 | 129 |
| 8 | 10 | 2549 | | | | 8373 | 5697 | 129 |
| 9 | 10 | 2533 | | | | 8301 | 5670 | 130 |
| 10 | 10 | 2041 | 508 | | | 8518 | 6024 | 120 |
| 11 | 10 | 2057 | 508 | | | 8863 | 5996 | 120 |
| 12 | 10 | 2037 | 508 | | | 8718 | 5996 | 120 |
| 13 | 10 | 2538 | | | | 8482 | 6015 | 134 |
| 14 | 10 | 2538 | | | | 8455 | 567 | 133 |
| 15 | 10 | 2545 | | | | 8410 | 5679 | 134 |
| 16 | 10 | 2545 | | | | 8509 | 5652 | 131 |
| 17 | 10 | 2554 | | | | 8428 | 5724 | 128 |
| 18 | 10 | 2549 | | | | 8423 | 5729 | 131 |
| 19 | 6 | 1080 | | 245 | 333 | 4844 | 3379 | 72 |
| 20 | 9 | 1585 | 404 | | | 7167 | 5788 | 114 |
| 21 | 8 | 2055 | | | | 6350 | 4704 | 118 |
| 22 | 8 | 1436 | | 336 | 445 | 6450 | 4504 | 99 |
| 23 | 7.5 | 1912 | | | | 6046 | 4500 | 101 |
| 24 | 7 | 1894 | 315 | | | 2712 | 6436 | 133 |
| 25 | 6.25 | 1082 | 288 | | | 4736 | 4196 | 81 |
| 26 | 3 | 649 | 166 | | | 2295 | 1882 | 41 |
| 27 | 8 | 1091 | | | 1100 | 5371 | 5597 | 113 |

Figure 5:
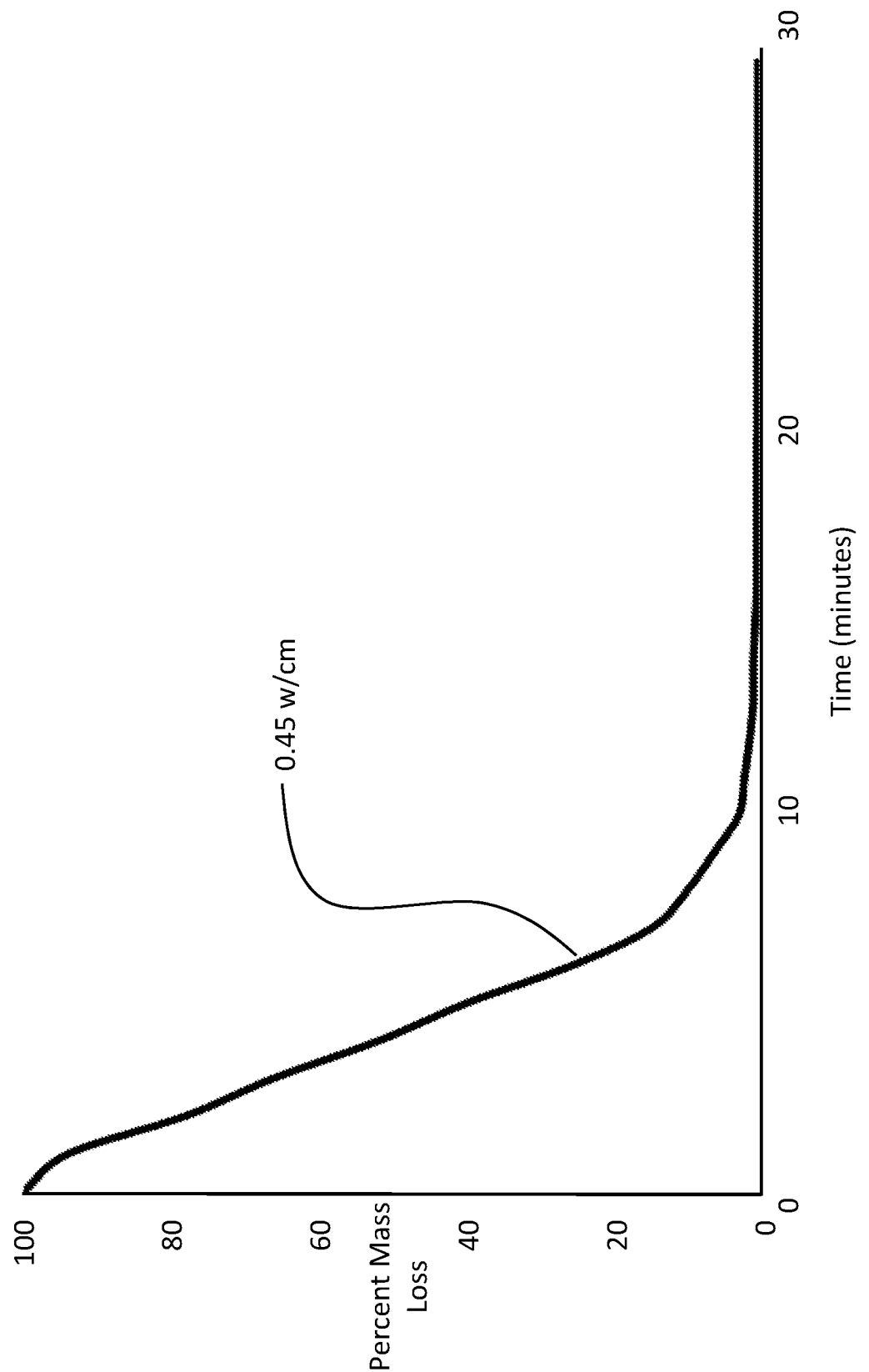
FIG. 5 depicts water loss when a Test Sample was heated with in an oven.

The method has also been tested by placing the Testing Container with Test Sample in an oven. The oven method is referred to as Configuration 2. The oven was set to operate at a maximum temperature of 815° C. For the purpose of the test results, a pan having a depth of 4.4 cm, a length of 22.9 cm and a width of 17.8 cm served as the Testing Container. The oven applied heat to the top and bottom of the Testing Container/Test Sample. FIG. 5 depicts the loss of mass for one sample when the Testing Container was placed in an oven as provided for Configuration 2.

Figure 6:
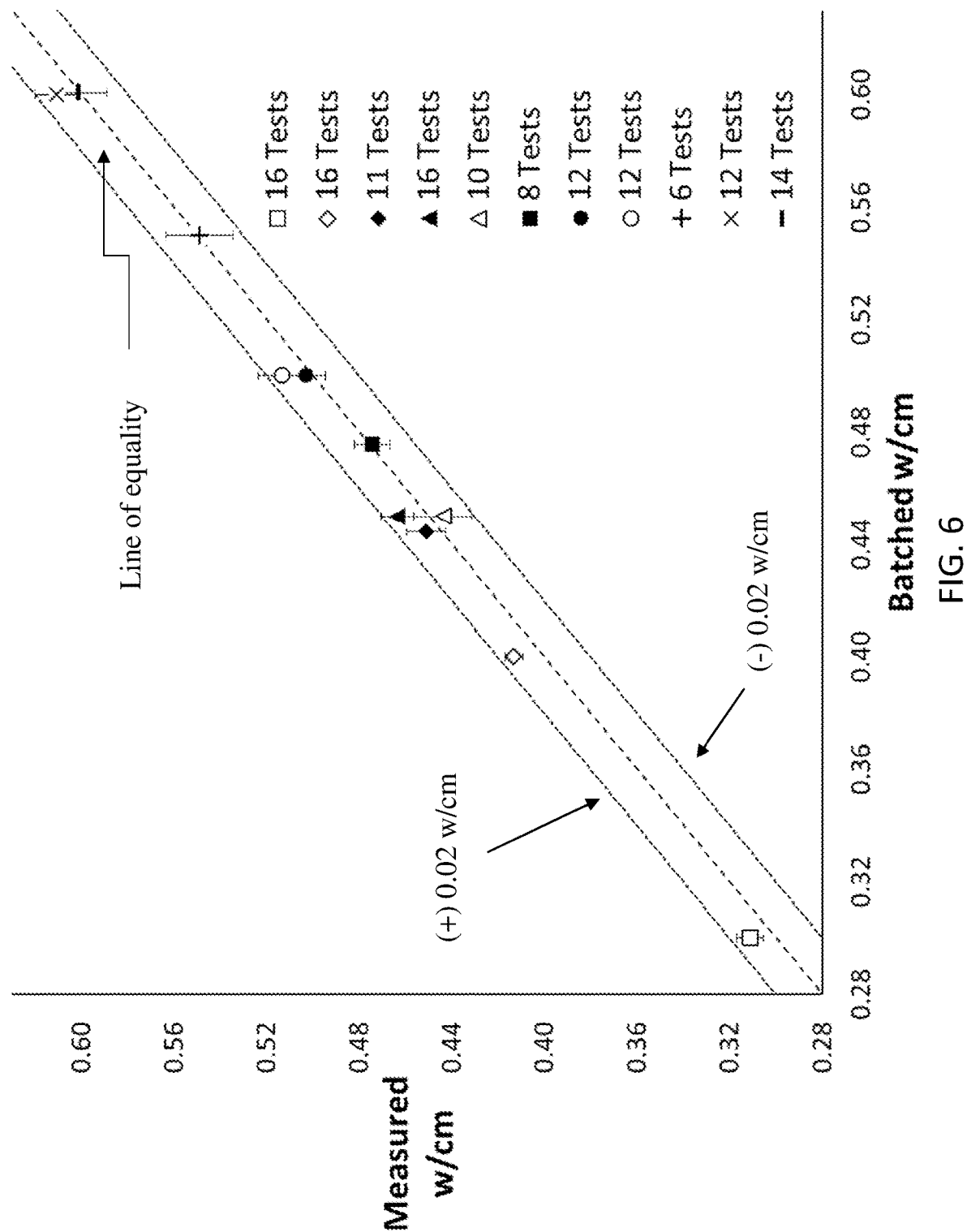
FIG. 6 depicts the test results of Table 5 when heating the Test Samples in an oven.

To evaluate Configuration 2, 133 samples were tested. For testing of Configuration 2, both pastes and concretes were evaluated. As reflected by Table 5, the concrete mixtures use Limestone 1 and Natural Sand 1. FIG. 6 graphically depicts the results reported in Table 5. FIG. 6 depicts the average and one standard deviation for each measured w/cm versus the batched w/cm. In this graph, all of the data is combined at each w/cm. A line of equality is included on the graph to show an exact match of the batched and the measured w/cm. The two lines on either side represent a +/−0.02 w/cm.

TABLE 5

| | | | Test Result for Configuration 2 | | | | |
|---|---|---|---|---|---|---|---|
| Tests | Batched w/cm | Avg. Measured w/cm | Difference Batched and Measured | Standard deviation | COV (%) | Coarse Aggregate Type | Fine Aggregate Type |
| 16 | 0.30 | 0.31 | −0.010 | 0.006 | 1.8 | — | — |
| 16 | 0.40 | 0.41 | −0.010 | 0.004 | 0.9 | — | — |
| 11 | 0.44 | 0.45 | −0.010 | 0.008 | 1.9 | Limestone 1 | Natural Sand 1 |
| 16 | 0.45 | 0.46 | −0.010 | 0.007 | 1.5 | — | — |
| 10 | 0.45 | 0.44 | 0.010 | 0.013 | 2.8 | Limestone 1 | Natural Sand 1 |
| 8 | 0.48 | 0.47 | 0.010 | 0.008 | 1.6 | Limestone 1 | Natural Sand 1 |
| 12 | 0.50 | 0.51 | −0.010 | 0.010 | 2.0 | — | — |
| 12 | 0.50 | 0.50 | 0.000 | 0.009 | 1.7 | Limestone 1 | Natural Sand 1 |
| 6 | 0.55 | 0.55 | 0.000 | 0.014 | 2.6 | Limestone 1 | Natural Sand 1 |
| 12 | 0.60 | 0.61 | −0.010 | 0.009 | 1.5 | — | — |
| 14 | 0.60 | 0.60 | 0.000 | 0.012 | 2.0 | Limestone 1 | Natural Sand 1 |

As reflected by Table 5, the average standard deviation for all measured w/cm is 0.009 for w/cm having values between 0.30 and 0.60. The average coefficient of variation (COV) for all 133 tests is 1.8%. This shows the test is precise and accurate, regardless of the test setup.

Figure 7:
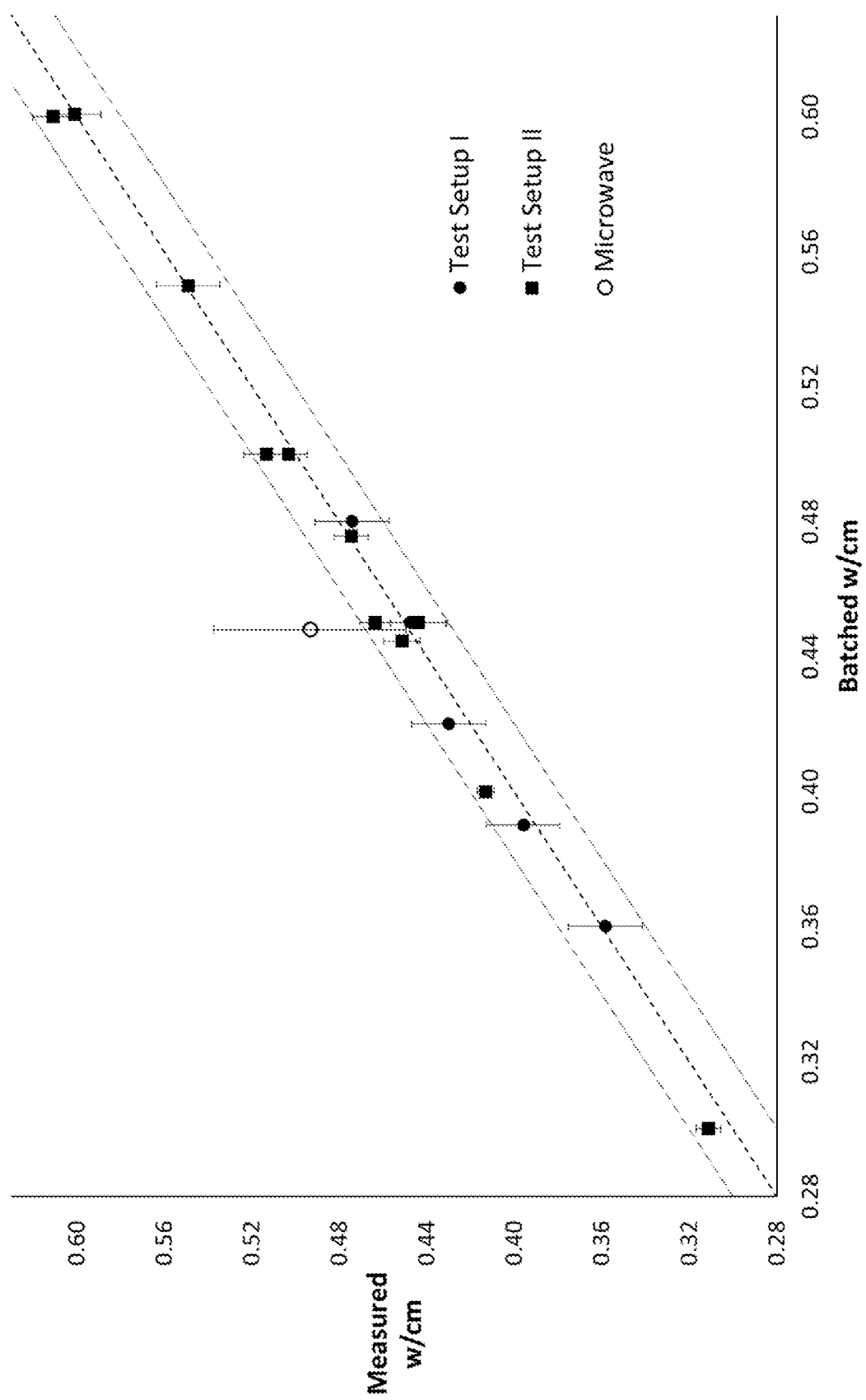
FIG. 7 depicts the average results for each test setup and also the average values for all the laboratory tests based on Configuration 1 and Configuration 2.

Further evidence of the accuracy of the described method for determining the w/cm is provided in Table 6 and FIG. 7. FIG. 7 graphically represents the values of Table 6 including one standard deviation results from each test setup. Table 6 provides the average for all laboratory tests conducted using both Configuration 1 and Configuration 2. As indicated in Table 6, the overall average measured w/cm values were within 0.01 of the calculated batch w/cm values. The COV for Configuration 1 is 3% while the COV for Configuration 2 is 1.8%. Additionally, when compared to tests performed using the currently available Microwave test, the above described method for determining the w/cm of fresh concrete provides significantly more accurate results in less time and with less labor. Thus, both Configuration 1 and 2 are precise, accurate and can be expected to provide satisfactory results in the lab and in the field.

TABLE 6

| | Average for All Laboratory Test Results | | | |
|---|---|---|---|---|
| | Average Difference Batched and Measured | Standard deviation | COV (%) | Time Required to complete test (min) |
| Test Setup I | 0.001 | 0.012 | 3.0 | 30 |
| Test Setup II | −0.004 | 0.009 | 1.8 | 12 |
| Microwave | −0.045 | 0.044 | 8.9 | 45 |

To determine the desired minimum and maximum sample volume range suitable for the Test Samples multiple tests were carried out on Test Samples having a w/cm of 0.45. Nine samples of varying volumes were tested as reported in Table 7 below. Based on the results reported on Table 7, the disclosed method can be practiced on Test Samples having as little as 1200 cm$^3$ and as much as 7000 cm$^3$. In most instances, Test Samples will have volumes between about 1200 cm$^3$ and about 6000 cm$^3$. The preferred volume range may vary depending on the heating apparatus available and the Test Container used. However, preferred test volumes will generally be between about 1600 cm$^3$ and about 1900 cm$^3$. For comparison, the sample volume commonly used for the microwave oven test method is 694 cm$^3$ according to AASHTO T318 test method.

TABLE 7

| | | Volume Testing at w/cm of 0.45 | | | | | | |
|---|---|---|---|---|---|---|---|---|
| Number Of Samples | Cylinder Size (in.) | Sample Volume (cm$^3$) | Avg. Density (kg/m$^3$) | Standard Deviation (kg/m$^3$) | Density COV (%) | Average Measured w/cm | Standard Deviation | Measured w/cm COV (%) |
| 9 | 3 × 6 | 694 | 2412.4 | 51.3 | 2.1 | 0.42 | 0.022 | 5.2 |
| 9 | 4 × 4 | 824 | 2410.8 | 22.4 | 0.9 | 0.44 | 0.021 | 4.8 |
| 9 | 4 × 6 | 1236 | 2425.2 | 12.6 | 0.5 | 0.45 | 0.022 | 4.9 |
| 9 | 4 × 8 | 1648 | 2428.4 | 4.8 | 0.2 | 0.45 | 0.010 | 2.2 |
| 9 | 6 × 4 | 1852 | 2428.4 | 8.0 | 0.3 | 0.45 | 0.010 | 2.2 |
| 9 | 6 × 12 | 5559 | 2418.8 | 11.2 | 0.5 | 0.44 | 0.011 | 2.5 |
| 9 | 8 × 8.8 | 7079 | 2423.6 | 8.0 | 0.3 | | | |

Finally, for completeness of data, Table 8 provides analysis of the oxides in the binder used during the laboratory testing and Table 9 below provides information on the aggregates used during laboratory testing.

TABLE 8

Binder Oxide Analysis

| Oxide % | SiO$_2$ | Al$_2$O$_3$ | Fe$_2$O$_3$ | CaO | MgO | SO$_3$ | Na$_2$O | K$_2$O | C$_3$S | C$_2$S | C$_3$A | C$_4$AF |
|---|---|---|---|---|---|---|---|---|---|---|---|---|
| Binder | 21.1 | 4.7 | 2.6 | 62.1 | 2.4 | 3.2 | 0.2 | 0.3 | 57 | 18 | 8.2 | 7.8 |

TABLE 9

Tested Aggregate Summary

| Aggregate Type | Size | Specific Gravity | Absorption (%) | State |
|---|---|---|---|---|
| Dolomitic Limestone | Coarse | 2.42 | 4.69 | IA |
| Gabbro | Coarse | 2.81 | 0.2 | OK |
| Glacial Till 1 | Coarse | 2.67 | 1.52 | MN |
| Glacial Till 2 | Coarse | 2.68 | 0.81 | MN |
| Granite 1 | Coarse | 2.59 | 1.06 | MN |
| Granite 2 | Coarse | 2.75 | 0.46 | OK |
| Limestone 1 | Coarse | 2.67 | 0.70 | OK |
| Limestone 2 | Coarse | 2.67 | 0.64 | OK |
| Limestone 3 | Coarse | 2.85 | 0.76 | OK |
| Limestone 4 | Coarse | 2.70 | 0.68 | OK |
| Limestone 5 | Coarse | 2.76 | 0.72 | OK |
| Limestone 6 | Coarse | 2.62 | 0.40 | KS |
| Limestone 7 | Coarse | 2.63 | 1.70 | KS |
| Limestone 8 | Coarse | 2.67 | 0.30 | KS |
| Limestone 9 | Coarse | 2.67 | 1.80 | KS |
| Limestone 10 | Coarse | 2.69 | 0.70 | KS |
| Quartzite-Granite 1 | Coarse | 2.66 | 0.66 | MN |
| Quartzite-Granite 2 | Coarse | 2.75 | 0.51 | GA |
| Sandstone | Coarse | 2.55 | 1.20 | AR |
| Manufactured Sand | Fine | 2.76 | 1.05 | OK |
| Natural Sand 1 | Fine | 2.62 | 0.64 | OK |
| Natural Sand 2 | Fine | 2.61 | 0.76 | OK |
| Natural Sand 3 | Fine | 2.64 | 0.34 | OK |
| Natural Sand 4 | Fine | 2.62 | 0.40 | KS |
| Natural Sand 5 | Fine | 2.62 | 0.20 | KS |

While Configurations 1 and 2 have been described for the heating portion of the described method, other configurations can be used to heat and remove water from the Test Sample. For example, Configuration 1 may be modified by removing either the heating element positioned above the Test Sample of the hot plate on which the Testing Container may be removed. Likewise, other oven configurations may be used in place of the oven described in Configuration 2.

Other embodiments of the present invention will be apparent to one skilled in the art. As such, the foregoing description merely enables and describes the general uses and methods of the present invention. Accordingly, the following claims define the true scope of the present invention.

We claim:

1. A method for determining the water content in a fresh concrete mixture, the method comprising:
   providing a test sample of fresh concrete mixture, said test sample of fresh concrete mixture comprising binder, water and aggregates;
   determining the mass of the test sample;
   determining the volume of air in the test sample;
   determining the absolute volume of the test sample;
   using the absorption capacity of the aggregates, determine the mass of water contributed by the aggregates in the test sample of the fresh concrete mixture;
   removing all evaporable water from the test sample without decomposing the aggregate portion of the test sample by heating the test sample in an environment having a temperature of about 100° to about 1400° C.
   while monitoring the weight of the test sample during the heating of the test sample;
   stopping the heating of the test sample when the weight of the test sample varies by less than two grams between successive two-minute weight readings;
   determining the mass of the test sample;
   determining the mass of water removed from the test sample; and,
   determining the mass of water in the fresh concrete mixture by subtracting the determined mass of water contributed by the aggregate in the test sample of fresh concrete mixture from the mass of water removed from the test sample to provide the mass of water in the fresh concrete mixture.

2. The method of claim 1, wherein the step of removing water from the test sample requires less than 60 minutes and provides for removal of all evaporable water without decomposing the aggregate portion of the test sample.

3. The method of claim 1, wherein the test sample is a portion of a larger batch of fresh concrete and further comprising:
   after preparing the larger batch of fresh concrete, monitoring the degree of hydration within the larger batch of fresh concrete or the test sample to determine when the degree of hydration has reached 2%; and,
   initiating the step of heating the test sample to remove water prior to or upon detecting a change in the degree of hydration of 2% within the larger batch of fresh concrete or the test sample.

4. The method of claim 1, wherein the test sample is a portion of a larger batch of fresh concrete and wherein the step of heating the test sample begins within five hours of the preparation of the larger batch of fresh concrete.

5. The method of claim 1, wherein the test sample is a portion of a larger batch of fresh concrete and wherein the step of heating the test sample begins at or prior to the larger batch of fresh concreter achieving a degree of hydration of 2%.

6. The method of claim 1, wherein said test sample has a volume between about of about 1200 cm$^3$ to about 7000 cm$^3$.

7. A method for determining the water to binder ratio of a fresh concrete mixture, the method comprising:
   providing a test sample of fresh concrete mixture, said test sample of fresh concrete mixture comprising binder, water and aggregates;
   determining the mass of the test sample;
   determining the volume of air in the test sample;
   determining the absolute volume of the test sample;
   using the absorption capacity of the aggregates, determine the mass of water contributed by the aggregates in the test sample of the fresh concrete mixture;
   removing all evaporable water from the test sample without decomposing the aggregate portion of the test sample by heating the test sample in an environment having a temperature of about 100° to about 1400° C. while monitoring the weight of the test sample during the heating of the test sample;

stopping the heating of the test sample when the weight of the test sample varies by less than two grams between successive two-minute weight readings;

determining the mass of the test sample;

determining the mass of water removed from the test sample;

determining the mass of water in the fresh concrete mixture by subtracting the determined mass of water contributed by the aggregate in the test sample of fresh concrete mixture from the mass of water removed from the test sample to provide the mass of water in the fresh concrete mixture; and, determining the water to binder ratio by dividing the mass of water in the test sample of fresh concrete mixture by the mass of the binder in the test sample.

8. The method of claim 7, wherein the step of removing water from the test sample requires less than 60 minutes and provides for removal of all evaporable water without decomposing the aggregate portion of the test sample.

9. The method of claim 7, wherein the test sample is a portion of a larger batch of fresh concrete and further comprising:

after preparing the larger batch of fresh concrete monitoring the degree of hydration within the larger batch of fresh concrete or the test sample to determine when the degree of hydration has reached 2%; and, initiating the step of heating the test sample to remove water prior to or upon detecting a change in the degree of hydration of 2% within the larger batch of fresh concrete or the test sample.

10. The method of claim 7, wherein the test sample is a portion of a larger batch of fresh concrete and wherein the step of heating the test sample begins within five hours of the preparation of the larger batch of fresh concrete.

11. The method of claim 7, wherein the test sample is a portion of a larger batch of fresh concrete and wherein the step of heating the test sample begins at or prior to the larger batch of fresh concrete achieving a degree of hydration of 2%.

12. The method of claim 7, wherein said test sample has a volume between about of about 1200 $cm^3$ to about 7000 $cm^3$.

13. A method for determining the water content in a fresh concrete mixture, the method comprising:

providing a test sample of fresh concrete mixture, said test sample of fresh concrete mixture comprising binder, water and aggregates;

determining the mass of the test sample;

determining the volume of air in the test sample;

determining the absolute volume of the test sample;

using the absorption capacity of the aggregates, determine the mass of water contributed by the aggregates in the test sample of the fresh concrete mixture;

removing all evaporable water from the test sample by heating the test sample in an environment having a temperature which will decompose the aggregates C while monitoring the weight of the test sample during the heating of the test sample;

stopping the heating of the test sample when the weight of the test sample varies by less than two grams between successive two-minute weight readings;

determining the mass of the test sample;

determining the mass of water removed from the test sample; and, determining the mass of water in the fresh concrete mixture by subtracting the determined mass of water contributed by the aggregate in the test sample of fresh concrete mixture from the mass of water removed from the test sample to provide the mass of water in the fresh concrete mixture.

14. The method of claim 13, wherein the step of removing all evaporable water continues for about 1 minute to about 20 minutes thereby removing all water from the test sample.

15. A method for determining the water to binder ratio of a fresh concrete mixture, the method comprising:

providing a test sample of fresh concrete mixture, said test sample of fresh concrete mixture comprising binder, water and aggregates;

determining the mass of the test sample;

determining the volume of air in the test sample;

determining the absolute volume of the test sample;

using the absorption capacity of the aggregates, determine the mass of water contributed by the aggregates in the test sample of the fresh concrete mixture;

removing all evaporable water from the test sample by heating the test sample in an environment having a temperature which will decompose the aggregates;

following removal of all water from the test sample determining the mass of the test sample;

determining the mass of water removed from the test sample;

determining the mass of water in the fresh concrete mixture by subtracting the determined mass of water contributed by the aggregate in the test sample of fresh concrete mixture from the mass of water removed from the test sample to provide the mass of water in the fresh concrete mixture; and, determining the water to binder ratio by dividing the mass of water in the test sample of fresh concrete mixture by the mass of the binder in the test sample.

16. The method of claim 15, wherein the step of removing all evaporable water continues for about 1 minute to about 20 minutes thereby removing all water from the test sample.

17. The method of claim 15, wherein the step of removing all evaporable water from the test sample further comprises the steps of:

monitoring the weight of the test sample during the heating of the test sample;

stopping the heating step when the weight of the test sample varies by less than two grams between successive two-minute weight readings.

\* \* \* \* \*